United States Patent [19]
Kendell

[11] Patent Number: 5,190,534
[45] Date of Patent: Mar. 2, 1993

[54] PREFILLED STERILANT FLUID RELEASABLE COUPLING CONNECTOR APPARATUS FOR CATHETER APPLICATIONS

[75] Inventor: Lamar C. Kendell, Ogden, Utah
[73] Assignee: DelMed, Inc., Ogden, Utah
[21] Appl. No.: 624,142
[22] Filed: Dec. 7, 1990
[51] Int. Cl.$^5$ ............................................. A61M 5/178
[52] U.S. Cl. ................................. 604/905; 604/283; 604/4; 604/29; 604/30
[58] Field of Search .................. 604/905, 283, 4–6, 604/29, 30

[56] References Cited

U.S. PATENT DOCUMENTS

| | | | |
|---|---|---|---|
| 3,484,121 | 9/1966 | Quinton | 285/242 |
| 4,294,250 | 10/1981 | Dennehey | 128/247 |
| 4,369,781 | 1/1983 | Gilson et al. | 604/905 |
| 4,402,691 | 9/1983 | Rosenthal et al. | 604/411 |
| 4,432,764 | 2/1984 | Lopez | 604/283 |
| 4,439,188 | 3/1984 | Dennehey et al. | 604/283 |
| 4,440,207 | 4/1984 | Genatempo et al. | 150/52 |
| 4,452,473 | 6/1984 | Ruschke | 604/905 |
| 4,511,359 | 4/1985 | Vaillancourt | 604/411 |
| 4,786,281 | 11/1988 | Valentini et al. | 604/256 |
| 4,810,241 | 3/1989 | Rogers | 604/28 |
| 4,981,469 | 1/1991 | Whitehouse et al. | 604/86 |
| 4,991,629 | 2/1991 | Ernesto et al. | 604/905 |
| 5,047,021 | 9/1991 | Utterberg | 604/283 |
| 5,053,015 | 10/1991 | Gross | 604/167 |
| 5,057,093 | 10/1991 | Clegg et al. | 604/283 |
| 5,088,984 | 2/1992 | Fields | 604/167 |

FOREIGN PATENT DOCUMENTS
2067075 7/1981 Fed. Rep. of Germany.

*Primary Examiner*—Robert A. Hafer
*Assistant Examiner*—Kerry Owens
*Attorney, Agent, or Firm*—Robert H. Falk; Henry Croskell; Tom R. Vestal

[57] ABSTRACT

A releasable coupling connector apparatus for catheter applications is provided wherein the connector is partially filled wtih anti-infective solution during manufacture and capped so that a patient or medical technician does not have the task of opening the fluid pathway and introducing the anti-infective solution at point of use into the connector apparatus. The connector apparatus being partially filled with anti-infective solution and capped during manufacture is further sterilized by Gamma radiation in order to eliminate any organism resistant to the anti-infective solution. The releasable coupling connector apparatus provides the first practical double seal connector means wherein a double seal connector defining dual sterilant liquid containing chambers for use with catheter applications and particularly with CAPD whereby sterilization is assuredly and easily achieved by an impaired, unskilled patient even under adverse conditions.

17 Claims, 3 Drawing Sheets

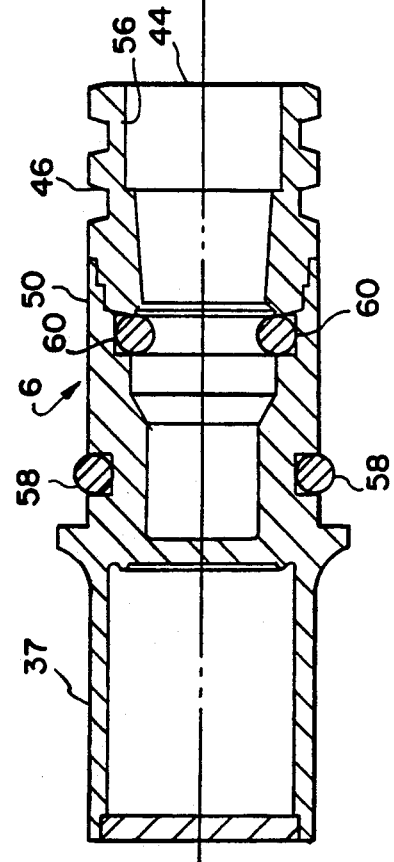
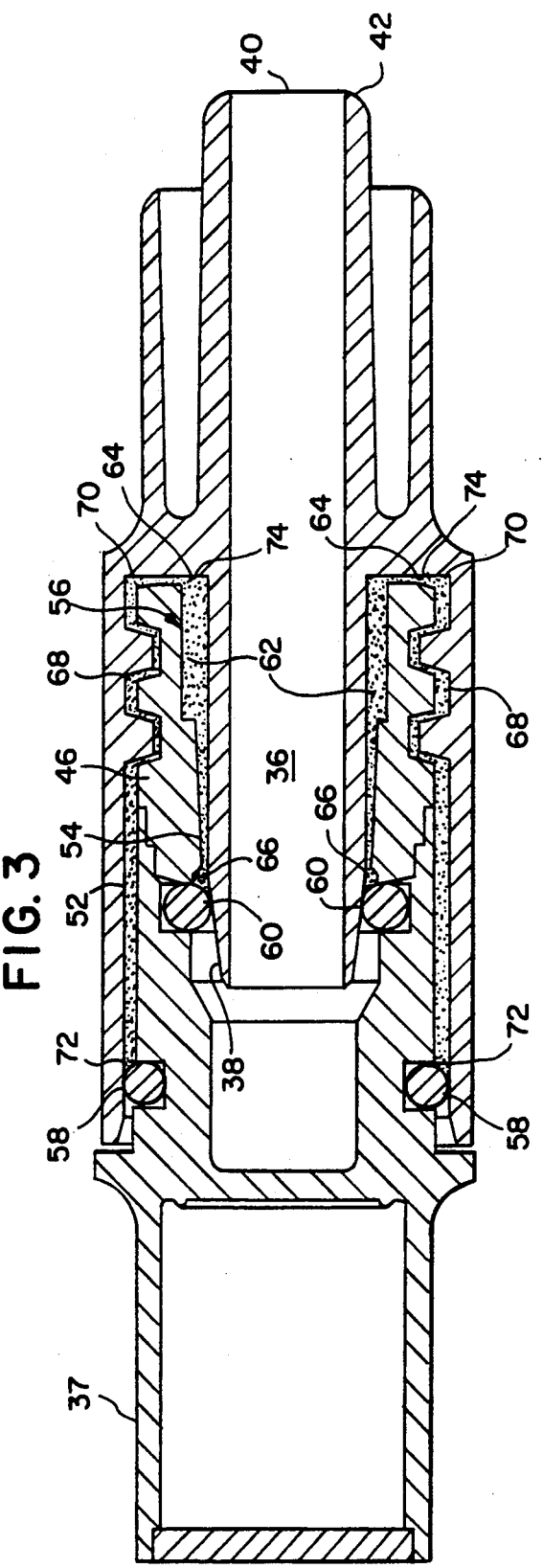

PREFILLED STERILANT FLUID RELEASABLE COUPLING CONNECTOR APPARATUS FOR CATHETER APPLICATIONS

FIELD OF THE INVENTION

This invention relates to a prefilled fluid sterilant barrier connector for the administration of sterile medical solutions and to a method for assuring that connections for the medical solutions or body fluids are capable of being connected and maintained in a sterile or an antiseptic condition.

In another aspect, the invention relates to a prepackaged connector having a sterile barrier defined by a connector and cap portion wherein the sterilant barrier can be maintained from manufacturer through connection with a patient catheter. In yet another aspect, the invention relates to a sterile connector apparatus for releasably coupling a first and second length of tubing and communicating the tubing interior for passage of sterile medical solutions or body fluids. Other aspects of the invention relate to the use of prefill sterilant fluid coupling connector apparatus and method for performing Continuous Ambulatory Peritoneal Dialysis (CAPD) wherein the sterilant barrier is maintained from manufacturer through use application.

BACKGROUND OF THE INVENTION

A. The Importance of Sterility in Dialysis Connections

Typical medical connectors used widely in modern medical practices are connectors for solution containers, administration sets and catheters. Sterile medical solutions such as for intraveneous feeding, transfusions, peritoneal dialysis and the like, are frequently administered to patients through a fluid conduit, a portion of which may be surgically implanted in the body. Medical procedures require a connection where the bacterial population is minimized because in such cases, an in-dwelling conduit, such as a sterile cannula, having one end located within the body has the other or second end remaining outside the body for connection to fluid administration conduit tubing. The medical solutions are commercially available packaged in containers such as flexible plastic bags or glass bottles and separate sterile, plastic disposable administration tubing is used to pass the contents of such bags through the in-dwelling conduit into the patient's body. Likewise, such separate sterile plastic disposable administration tubing sets are utilized for expelling body fluids and/or recirculating body fluids after toxin removal. The bag, administration tubing and in-dwelling conduit must form a sterile fluid circuit. Therefore, it is essential that any connection between the conduit circuit elements must be established and maintained in an antiseptic condition to avoid contamination.

Medical, biological, pharmaceutical research and medical care most frequently require that not any bacterium or other infectious agents such as yeast, fungus, virus and the like and minimum disinfection liquids penetrate into a system of mutually connected units such as tubings, bottles, containers, catheters and infusion means as well as drains.

Of particular importance in the medical care area is in the treatment of patients experiencing partial or total kidney failure. The most widely used method of kidney dialysis for treatment of kidney failure i.e. renal disease is hemodialysis. In hemodialysis the patient's blood is cleansed by passing the blood through an artificial kidney and a kidney dialysis machine. By the process of diffusion across the semipermeable membrane in the artificial kidney, impurities and toxins are removed from the patient's blood to thereby perform a function of the patient's natural kidneys. Hemodialysis is required several times a week, each dialysis requiring several hours in a dialysis center wherein the patient is tied to the machine through arterial blood lines which convey the blood to and from the kidney machine.

Another treatment of renal disease is through a procedure known as intermittent peritoneal dialysis. In this procedure, a dialysis solution is infused into the patient's peritoneal cavity by means of tubing and a catheter. The peritoneum, which defines a peritoneal cavity, contains many small blood vessels and capillary beds which act as a natural semipermeable membrane. The natural membrane may be contrasted with the artificial membrane used in hemodialysis. In both cases, however, impurities and toxins in the blood are removed by diffusion across a membrane such as a cellulose membrane of the artificial kidney or a peritoneal natural membrane of the peritoneal cavity. Dialysis solutions remain in the patient's peritoneal cavity in intermittent peritoneal dialysis for a time sufficient for blood impurities to be removed by diffusion across the peritoneal membrane into the dialysis solution. The impurity containing dialysis solution then is drained from the peritoneal cavity by means of a catheter and tubing and a fresh supply of dialysis solution is infused. Intermittent peritoneal dialysis uses pumps or other auxiliary equipment to which the patient is again generally tied during dialysis, i.e. the patient must remain sedentary.

B. Problems of Sterilizing CAPD Connectors

Continuous Ambulatory Peritoneal Dialysis (CAPD) is another type of peritoneal dialysis which uses the peritoneum as a semipermeable membrane. Note U.S. Pat. No. 4,239,041 to Popovich and Moncrief. In CAPD multiple daily exchanges of sterile fluid are performed by the patient through a flexible in-dwelling cannula which is surgically implanted into the peritoneal cavity and sutured in place so that one end of the cannula is located within the cavity and the second end, or junction side end, remains outside the body cavity to form a convenient, reusable, sterile fluid conduit to the patient's peritoneal cavity. The administration tubing set is connected to the dialysis fluid containing bag by a plastic attachment at one end and to the in-dwelling flexible cannula with a special, comparatively permanent, sterile attachment at the second end. The CAPD procedure has the important advantage of enabling the patient to be ambulatory and conduct a normal routine during dialysis. The patient is not tied to a machine and only needs to be sedimentary only for the brief periods required to drain and infuse dialysis solution from and into the peritoneal cavity.

The CAPD procedure is intended to be a patient self-care process once the catheter is surgically implanted. It is important therefore that the apparatus involved including tubing solution container, tubing connectors and the like be simple and easy to use. In such self service and self treatment procedures, security of the system as well as anti-bacterial protection of the system is most important.

Very serious medical treatments require the use of permanently implanted catheters or cannulas having an end-fitting that is connected periodically or continuously to a machine, liquid supply reservoir or liquid receiving reservoir. Obviously it is essential that a connection be made antiseptically, particularly as the person undergoing such treatment is frequently in a fragile state of health. Even the slightest sepsis can introduce bacteria directly into the body of the patient, creating the possibility of a grave infection. Of the two main types of peritoneal dialysis inclusive of CAPD, the other method is intermittent peritoneal dialysis which is carried out in a hospital or clinic using machines that are connected by medical personnel to the patient's catheter for treatment. On the other hand, CAPD involves a connection made to the patient's catheter from a pouch supply carried directly on the patient. One problem with the CAPD method is that the subject's condition must be maintained by the patient rather than by trained medical personnel. Obviously, in such a situation experience has shown a great number of infections caused by non-aseptic procedures. The main problem is normally caused by the connection to the end fitting of the implanted catheter. The connection must seal perfectly, not allowing any foreign matter to enter the liquid stream which must pass through the connection, and must, of course, also prevent the liquid from leaking. Furthermore, this connection must be mechanically very strong so that it cannot be accidentally pulled open or apart.

It is desirable to provide a protective cap for medical connectors as well as antiseptic barriers within these connectors. For CAPD connector use in particular, the connectors need to be secure and to provide an anti-bacterial effect in the connector. During CAPD, a certain quantity of sterile dialysis fluid is brought from a plastic bag through a tubing system into the peritoneal cavity. After a period of some time, the fluid is transferred from the cavity back to a receiving bag, possibly the same bag. In the meantime, an osmotic equilibrium is accomplished between the waste substances accumulated in the blood of the uraemic patient and the dialysis fluid. By replacing the dialysis fluid with fresh dialysis fluid after several hours, one removes again and again a portion of the accumulated waste substances from the blood. As the dialysis fluid is changed four or five times a day, about 1,500 connections and the disconnections of dialysis bags are necessary per year. It is absolutely necessary to carry out a sterile connecting and disconnecting procedure. Since the dialysis fluid does not comprise white blood cells, it is clear that any infectious agents i.e. bacteria introduced during the connecting procedure, even if there are very few, may multiply unhindered inside the abdominal cavity i.e. the peritoneal cavity of the patient. A significant chance exists that one or more bacteria will enter one or more times a year, through the dialysis system, into the peritoneal cavity. This is an occurrence with a practice of CAPD, according to which about 60% of the patients suffer from peritonitis within two years after starting the CAPD treatment. In most cases the bacteria are infectious agents normally present in the patient environment and can be found in the dialysis fluid. In view of the fact that the treatment takes place at home where the patients themselves will carry out the replacements and connections, a simple connector system is necessary which must have or give 100% security. Any contact of the connectors with the hand or clothing should not give rise to contamination of the dialysis fluid. No new infectious agent should be allowed to penetrate the system through the connector processes.

In other medical treatments it seems the treatments are somewhat less sensitive than CAPD, however, it is still desirable that contamination be held at a minimum. If infectious agents are introduced into the bloodstream during the administration of intraveneous fluids or medication, they normally come in contact with $10^7$ white blood cells per milliliter of blood which strongly counteracts the multiplication. However, there is a considerable number of patients suffering from a serious reduction in the number of immunological activity of white blood cells for example, the treatment of some cancer patients and acquired immune deficiency patients. The introduction of one single bacterium in the body of this group of patients can cause perilous infections.

Presently various types of connector assemblies attempt awkwardly to address these problems. However, not one of these types meet the conditions that not any infectious agent is allowed to penetrate the tubing or containers to be connected. Several connector apparatus approaches have been used in an attempt to solve this problem. In one type, a barrier connector assembly, the female part is closed by a membrane. To achieve the connection, the male part not covered by a barrier, will bring a small quantity of non-sterile air into the tubing to be connected, while a small but non-neglected quantity of germicidal fluid will enter the tubing each time, when, as is usually done, both connectors are sprayed with the germicidal fluid.

In another type of barrier connector assembly, both connectors are provided with a deformable barrier and before connecting these connectors the barriers are first brought into contact with each other, after which the fixation points of these barriers will not change their mutual position. One of the connectors comprises a telescopically movable penetration tube which during the coupling of connectors is pushed through both barriers and is slid with its front end into the other connector. An example of this type of connector assembly is disclosed in U.S. Pat. No. 4,334,551. In coupling the connectors, a sterile connection might be achieved if both barriers would have been sprayed beforehand with a sterilizing liquid, however, there is the risk that the penetration tube after penetrating the first barrier, pushes away the second barrier and unsterile air would be sucked into the space created by both barriers. However, a more serious drawback is that during the disconnection procedures the barriers are pulled loose from each other by the retracking penetration tube so that unsterile air is sucked between both barriers which air could contaminate the outside of the penetration tube.

Other commercial attempts at minimizing environmental and touch contamination of connector apparatus awkwardly requires the patient remove povidone iodine antiseptic sponges from a container, separately removing sterile gauze sponges from another container or envelope, apply the swab dressing to the spike connector site and place the gauze sponge around the dressing after which the patient must peel the backing off, tape and separately apply it around the dressing and gauze sponges to hold same in place around the connection. Thus, not only must the patient make the tubing connection, inserting the male or spike portion of the connection, but the patient must then immediately manually carry out the several described steps to establish and maintain an antiseptic connection of the connector while connector remains exposed to the atmosphere. Although the components of the connector are provided in a kit, the components nevertheless require considerable handling resulting in technical difficulties which arise from attempting to hold the connection site away from any possible sources of contamination while simultaneously attempting to unpack the dressing and gauze and tape strips. The chance for mishandling and resulting contamination is increased. Moreover, the risk of touch contamination are considerably increased as well as touch contamination of various components such as the gauze sponges and the like. Accordingly, not all such prior art approaches are inconvenient, but these approaches leave much to be desired from the standpoint of the patient's safety.

The foregoing difficulties in attempting to utilize antiseptic sponges are addressed in U.S. Pat. No. 4,402,691 through the provision of an application of a firm plastic protection enclosure barrier device for surrounding the connection site and providing the site with an antiseptic barrier. The barrier device sometimes also identified as a clam shell approach is comprised of a contoured plastic housing formed by mating cavity halves joined along a hinge line, and absorbent member contained within the interior of the housing in a sealing tab attached to one of the housing halves for holding the two halves together when folded along the hinge line. In use, the absorbent member has antiseptic solution applied to the member and the housing is positioned to surround the connection site and sealed in place to form a surrounding protective area barrier in seal. Another prior art attempt in solving patient contamination either in CAPD applications or other catheter is provided in U.S. Pat. No. 4,432,764 wherein an antiseptic end cap for catheters is suggested in order to prove antiseptic catheter fittings. An antisepticizing device comprising a cap having a formation adapted to fit complementarily with the end fitting of the catheter and formed with a passage having one end communicating with the end fitting and therethrough with a catheter when the end fitting is fixed to the formation. A reservoir in the cap has a movable wall, and the other end of the passage opens into the reservoir which contains a body of antiseptic liquid. Means are provided for displacing the movable wall of the reservoir and thereby forcing the liquid through the passage into the catheter fitted to the formation.

Another antibacterial protective cap for connectors is provided in U.S. Pat. No. 4,440,207. A protective cap for the connector which securely receives and provides an antibacterial effect to the connector is provided wherein at least a portion of the protective cap interior is lined with an absorbent material which retains an antiseptic. The connector covered by the protective cap is thus placed in an anti-bacterial environment made possible by contact of the connector with the antiseptic-retaining absorbent material or from migration of the antiseptic or both. The protective cap is contemplated for use on solution container connectors and particularly connectors communicating with the patient in peritoneal dialysis procedures. The liquid antiseptic such as povidone iodine, retained in the absorbent material lining within the cap, provides the anti-bacterial effect.

In yet another attempt to avoid or to minimize danger of peritoneal infections in CAPD procedures is presented by U.S. Pat. No. 4,810,241. An ambulatory dialysis system connector is presented comprising a cylinder containing a disinfecting solution which continuously bathes the male and female connectors of a tube during use. A highly absorbent material is packed in the cylinder and saturated with a disinfectant and bathes the male and female connectors when connection is made and continually bathes the connector portions during use. A connection is provided by male fitting on the end of a tube connected to a container of dialysate fluid or in an abdominal opposing tube. The male connector is inserted into the female connector through the cylinder containing the absorbent material saturated with the disinfectant. The absorbent material is packed such that the male connector contacts the absorbent material during insertion to disinfect the opposing end simultaneously while connection is being made. Once the dialysate fluid is delivered to the patient through the connector, the tube may be pulled off the outer end of the male connector to remove the empty containers. The male connector is then sealed and capped.

C. Problems With the "Double Seal" Connector in CAPD

In yet another CAPD connector approach has been the luer lock assembly as presented in U.S. Pat. No. 4,346,703, a so-called "double seal" connector. The luer lock connection system provides for the transfer tube extending from the dialysis solution bag to transport through a first luer connector and the catheter tube extending from the patient's peritoneal cavity carries the luer lock connector. The connector is presented as achieving in the absence of liquid and maintaining an uncontaminated connection at the luer connector. The luer lock connector which is carried by the patient is presented as being relatively of a permanent type while the cooperating luer lock connector which is carried on the tubing extending from the solution container may be of a relatively disposable type. It is necessary that the luer lock connection be secure and that leakage be prevented in order to prevent contamination which could result in peritonitis. As an object, the luer lock connection device includes seal-type engagement between the male and the female luer lock connectors thus preventing leakage and maintaining water-tight bacteria barrier at the connection. The '703 patent at Col. 7, lines 6–17 mentions the possibility of adding a sterilant at point of use by the patient, but makes no teaching as to the amount of sterilant to be employed, or the difficulties in how the chamber of the male piece is to be filled, and to what degree.

In an illustrated embodiment the flexible tube has a luer connector at its distal end for connecting to a luer connector carried by the patient's tube. The luer connector at the disteal end and the patient's tube luer connector comprises a cooperating male luer lock connector and a female luer lock connector. The male luer connector has a central tubular portion defining an actual bore with at least a portion of the central tubular portion being enclosed by an outer sheath having a generally circular cross-sectional configuration. The outer sheath being internally threaded.

The female luer connector comprises a main tubular member which cooperatively engages the male luer central tubular portion to provide a form fit liquid seal. The main tubular member has an outwardly radially extending flange adjacent its disteal end. In one embodiment, the flange takes the form of a single annular outwardly extending member. In another embodiment an elastomeric member is carried by the female luer connector and is dimensioned and operable for providing a second liquid seal with the internal wall of the rigid outer sheath of the male connector to aid in maintaining a water-tight bacteria barrier at the luer lock connection. Further, the elastomeric member may be swabbed or the chamber defined by the outer sheath filled with a sterilizing agent by the patient which would aid in preventing contamination of the system. Here again the patient must manipulate swab, spray or fill a certain small apparatus during delicate procedures of reconnecting a CAPD process and apparatus step.

Clearly, antiseptic connectors and connections which also provide physical connection strength are needed by the medical and medical research industries for various applications inclusive of hemodialysis and peritoneal dialysis. Ease of operation for the CAPD patient is important, while need for minimizing environmental and touch contamination of the self serving patient is of paramount importance as indicated by the various apparatus and methodologies proposed by the prior art. The various approaches provide multiple components and steps even though provided in kit form, present multiple steps wherein contamination can occur in patient's self care techniques. Many of the patients who practice continuous ambulatory peritoneal dialysis have limited physical capacity because of poor eyesight, weaknesses, arthritis and the like. There continues to be a need for connector systems which avoid as many procedural steps as possible, while yet providing physical integrity of connection along with antiseptic environment whether used by children, geriatric patients or by professional medical personnel. In short, there has been and continues to be the strongest medical need in the art since at least as early as 1982, for a double seal connector easily adaptable for precision connection by an impaired patient under adverse circumstances, where the connection between male and female pieces is assuredly sterilized.

SUMMARY OF THE INVENTION

Applicant has achieved by means of the invention the first practicable double seal connector (Defining dual sterilant containing chambers) for use in CAPD, whereby sterilization is assuredly, easily and promptly achieved by an impaired and unskilled patient, even under adverse conditions. The disadvantages associated with the prior art attempts at providing antiseptic connectors and physically appropriate connections for sterile medical solution administration conduits are met through the provisions according to the invention, wherein a connector which is partially filled with antiseptic fluid during manufacture is capped so that the patient does not have the task of opening the fluid pathway, drawing the antiseptic into a dropper bottle, and placing the drops into the connector and subsequently making the connection. The methodology and apparatus of the invention add the antiseptic fluids prior to the point of use and seal the antiseptic fluids into the connector so that disinfecting and sterilizing properties are uniform in application and greatly ease the process of patient connection of tubing thereby eliminating the need for patients to apply the antiseptics independently. The male connector is partially filled with antiseptic fluid and sealed by a cap means. The cap means having inner and outer O-ring type seals which prevent the antiseptic from leaking out into the sterile fluid pathway or to the exterior portions of the connector. These two seals and the twist lock or threaded mating of male and female parts enable the antiseptic liquid to be applied at the point of manufacture, closed and sealed until the tubing set is connected to either the patient's catheter adapter or sterile bag of solution.

In another embodiment, the methodology and apparatus of the invention provides for gamma sterilization to eliminate contaminations by organisms resistant to the particular type of disinfectant used. The fact that the male connector is partially filled with disinfectant and sealed by cap means during manufacture, provides the only device wherein disinfectant is sealed in the unit and suitable for being sterilized by radiation. The manufacturing process and resulting apparatus allows for Gamma radiation sterilization of the fluid and closed connector giving absolute sterility to the connector rather than imperfect disinfecting action.

The antiseptic liquid or fluid sterilizing agent is maintained in a chamber defined by the cap means and the connector or by the male/female connectors in connected position with a U-shaped chamber terminating and sealed by respective elastomeric seals.

Continuous Ambulatory Peritoneal Dialysis apparatus inclusive of a solution container coupled through flexible tubing to a patient's tube which is in communication with the patient's peritoneal cavity is provided wherein the key to the apparatus is in the disconnection and reconnection of the flexible tubing extending from the patient's peritoneal cavity to sources of dialysis fluid. A permanent patient's tube extends from the connector on one end and a disposable tube carried by the dialysis solution container and/or drainage container on the other end of the connector. Semi-permeable tubing sets are included on both ends which carry a luer type connector, one connection is made with the patient's tube and the other is to the solution container. The flexible tubing which is designated to be connected semipermeably to the patient's tubing being replaced approximately once per month, however, the connection being disconnected and reconnected several times per day.

In one embodiment according to the invention the flexible tube has a luer connector at its distal end for connecting to a luer connector carried by the patient's tube. The luer connection at the distal end of the patient's tube comprises a cooperating male luer lock connector and a female luer lock connector. The male luer connector has a central tubular portion defining an axial bore with at least a portion of the central tube portion being enclosed by an outer sheath having a generally circular cross-sectional configuration. The outer sheath being internally threaded or providing other locking means.

The female luer connector comprises a main tubular member which cooperatively engages the male luer central tubular portion to provide in cooperation with a first elastomeric seal. The main tubular member has an outwardly radially extending flange adjacent its distal end. In one embodiment the flange takes a form of a single annular outwardly extending member. An elastomeric member, i.e. a second seal is also carried by the female luer connector and is dimensioned and operable for providing a second liquid seal with the internal wall of the rigid outer sheath of the male connector to maintain a fluid tight bacteria barrier at the luer lock connection. Further, the elastomeric O-ring members terminate at two spaced apart portions of a continuous chamber defined by the male and female members. Another embodiment is defined by a capped female seals bearing apparatus in cooperation with the male member of the male luer lock member connector.

In another embodiment according to the invention, the various seal means can be comprised of pliable plastic seal mean members or similar seal apparatus. The elastomeric O-rings can be substituted by pliable plastic to plastic filament type of seals. For example, sealing surfaces can be comprised of an undercut portion and compressable, pliable plastic seal members which function in the same way as O-rings presenting similar seal functionality.

The male and female luer lock connectors are each formed of an integral one-piece construction. The seal members such as a general elastomeric material having sufficient physical properties to avoid transport of water and other solvents utilized with the sterilizing agent. The connectors can be formed of stainless steel or titanium but are preferably of a resilient plastic material which is readily disposable. Clamp members can be constructed of clear or translucent thermoplastic materials such as acrylic or similar materials. The flexible tubing can be constructed of flexible polyvinyl chloride or other clear, flexible, translucent, thermoplastic materials inclusive of polypropylene, polyethylene, acrylonitrile, butadiene styrene and the like. A variety of materials may be utilized for the connectors, clamps, tubing, and solution bags without departing from the scope of the present invention.

BRIEF DESCRIPTION OF THE DRAWINGS

FIG. 2 is a longitudinal section exploded view showing a male luer connector in actual alignment and positioned for connection with a female luer connector cap, sterilizing fluid agent being added to the male luer connector before assembling.

FIG. 3 is a longitudinal assembled view of the male luer connector and the female luer connector cap of FIG. 2 shown engaged and joined defining a chamber which is filled with fluid sterilizing agent.

DETAILED DESCRIPTION OF THE PREFERRED EMBODIMENTS

Figure 1:
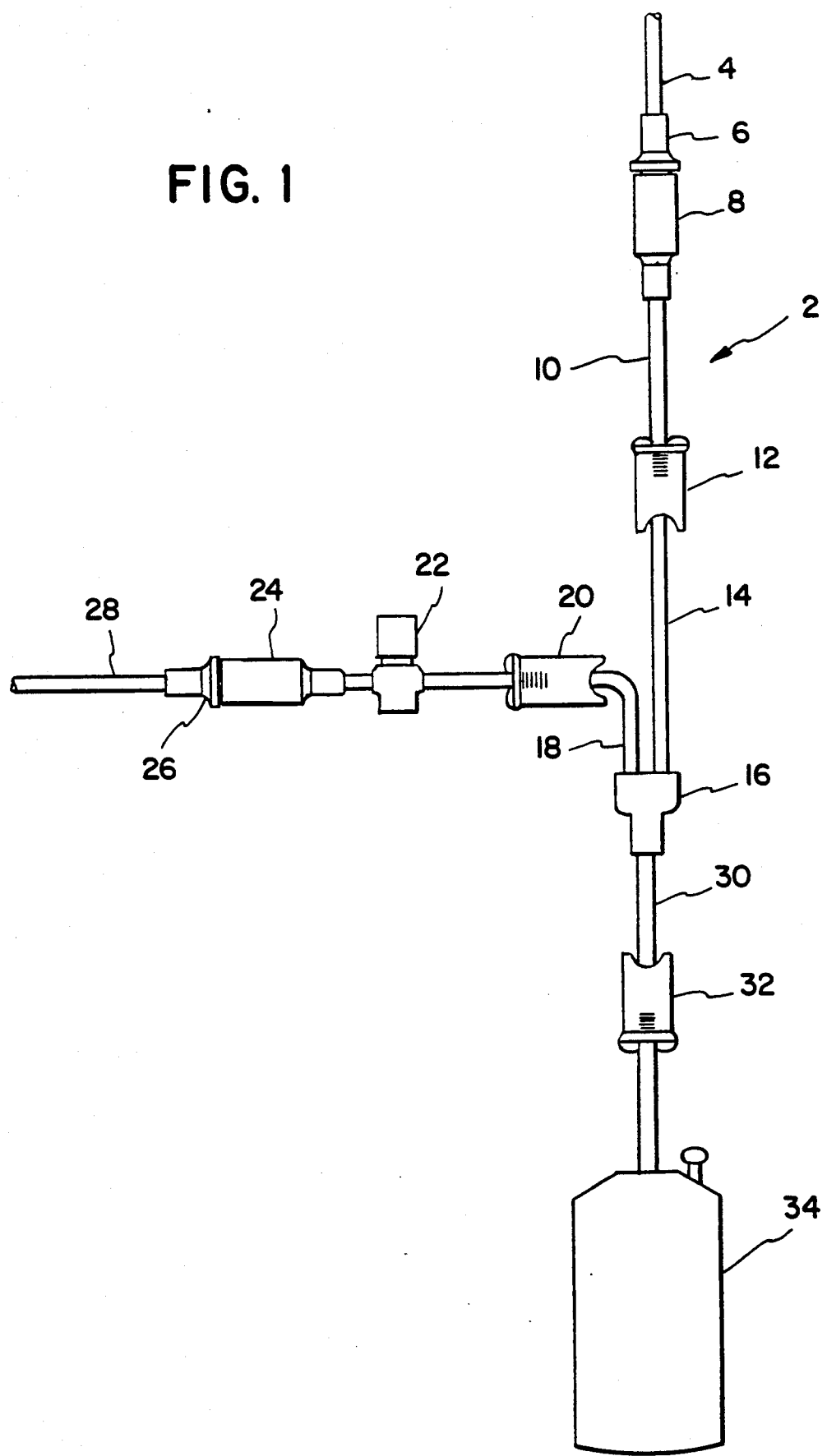
FIG. 1 is an overall schematic view of a Continuous Ambulatory Peritoneal Dialysis Disposable Freedom Set including drain, tubing set and the sterile connection combinations constructed in accordance with one embodiment of the present invention.

An overall schematic view is presented in FIG. 1 of a Continuous Ambulatory Peritoneal Dialysis Safelock ® Disposable Freedom Set ® 2 which includes drain bag tubing set and the sterile connectors combinations constructed in accordance with the invention. Flexible tubing 4 provides a conduit for dialysis solutions from a solution bag (not shown). Female luer lock connector 6 is presented at a distal end of tubing 4 from the solution bag. A male luer lock connector 8 is joined with the female luer lock connector 6 and flexible tubing 10 which connects the male luer connector with Y-tubing connector 16. Between the male luer lock connector 8 and the Y-tubing connector 16 is a manual clamp 12 and continuing tubing 14 from the clamp 12 to the Y-tubing connector 16. Flexible tubing 18 connects the Y-tubing connector 16 in a Y-configuration with manual clamp 20 and mechanical clamp 22. The flexible tubing 18 provides a conduit from the Y-tubing connector 16 to the male luer connector 24 which is at the distal end of tubing 18. Female luer connector 26 is at the distal end of a patient catheter tube 28 thus completing the tubing conduit flow of dialysis solution to the peritoneal cavity of the patient. Extending from the Y-tubing connector 16 is a drain tube 30 which is in communication with drain bag 34 with a manual clamp 32 positioned between the Y-tubing connector 16 and the drain bag 34. Upon completion of the CAPD peritoneal dialysis patient cycle, manipulation of the various clamps of tubing 18, tubing 14 and tubing 30 will allow the drainage of the patient's peritoneal cavity of the spent dialysis fluid containing the body waste materials achieved through membrane separations which have occurred within the peritoneal cavity. The drainage is into drain bag 34 for disposal purposes.

Referring to FIG. 2, a longitudinal sectional exploded view showing a male luer connector 24 in actual alignment in position for connection with a female luer connector cap 37. The male luer connector 24 is comprised of a male central tubular portion 36 and a tubular sheath portion 38 sharing a common actual bore 40. The actual bore 40 has an open end 42 which is generally connected to tubing means. The male central tubular portion 36 inclusive of the tubular sheath portion 38 are sized to be received and locked into position with female hollow tubular portion 44 using thread means 46 or other locking means. The female cap 37 as shown in Figure 2 provides female outer side surface 50 of female hollow tubular portion 44. The interior surface 52 of male tubular sheath portion 38 fits over the female outer side surface 50 of the female hollow tubular portion 44. The outer surface 54 of the male central tubular portion 36 penetrates into and is received by female hollow tubular portion 44 and lockable therein through thread means 46. The female interior surface 56 of female hollow tubular portion 44 receives the outer side surface 54. Seal means 58 are provided to seal the inner surface 52 of tubular sheath portion 38 against the female outer surface 50 thereby forming a first liquid seal. A second liquid seal is formed through the seal means 60 which seals the female inner surface 56 of female hollow tubular portion 44 against outer surface 54 of the male central tubular portion 36.

FIG. 3 presents a longitudinal view of the male lunar connector 24 assembled with female lunar connector cap 37 of FIG. 2 wherein the female cap 37 and male connector 24 are joined and engaged defining an inner annular portion 62 having an annular first end 64 and an annular second end 66. An outer annular portion 68 is also defined with an outer annular first end 70 and an outer annular second end 72. The inner and outer annular portion 62 and 68 are joined and communicate forming a sterilant fluid receiving chamber 74. The sterilant fluid receiving chamber 74 comprised of a communicating inner annular portion 62 and outer annular portion 68 which terminate with an inner annular portion seal means 60 and an outer annular portion seal means 58.

Figure 4:
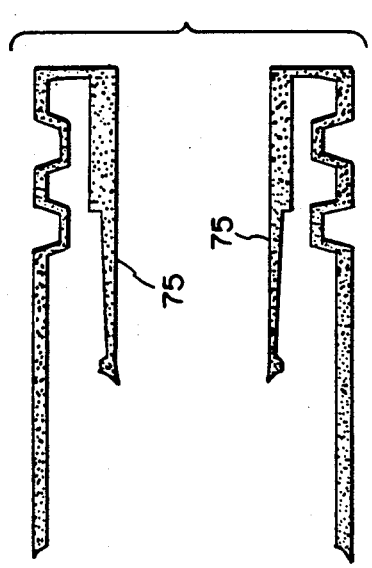
FIG. 4 is an elevational view of the fluid sterilizing agent chamber of FIG. 3 shown in isolation.

An elevational view in isolation of the sterilant fluid receiving chamber 74 is presented in FIG. 4. The sterilant fluid receiving chamber is filled with a sufficient amount of fluid sterilizing agent 75 to fill the receiving chamber 74. The fluid sterilizing agent remains in place during use as a result of the male luer clamp 24 and female luer clamp 26 mating inclusive of the outer annular seal means 58 and inner annular seal means 60 contained within the female luer connector.

Figure 5:
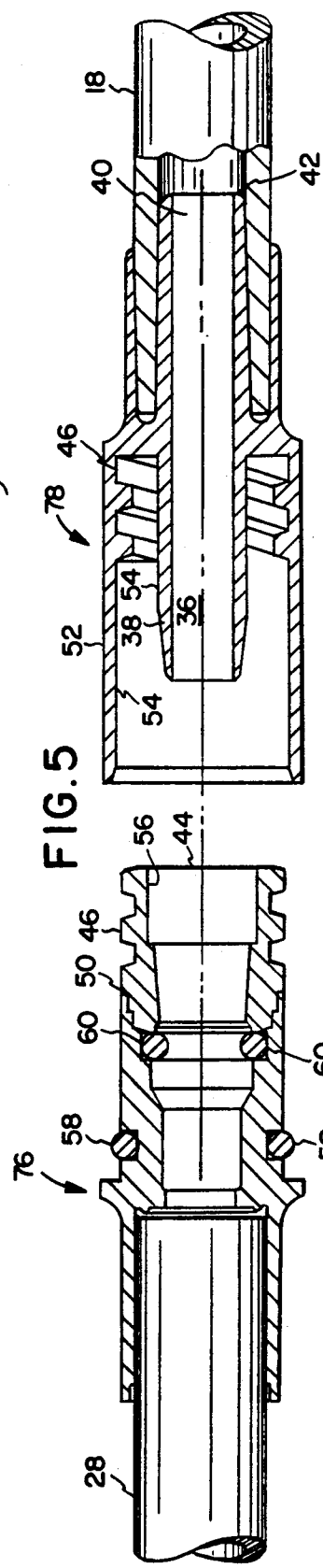
FIG. 5 is a longitudinal sectional exploded view showing the male luer connector of FIG. 2 including tubing connection in place, the male luer connector in actual alignment and position for connection with a female luer connector with the cap of FIG. 2 removed, the female luer connector including a tubing connection, when connected the male and female connectors defining a continuous fluid passage from tubing to tubing and the sterilizing fluid agent chamber of FIG. 4.
Figure 6:
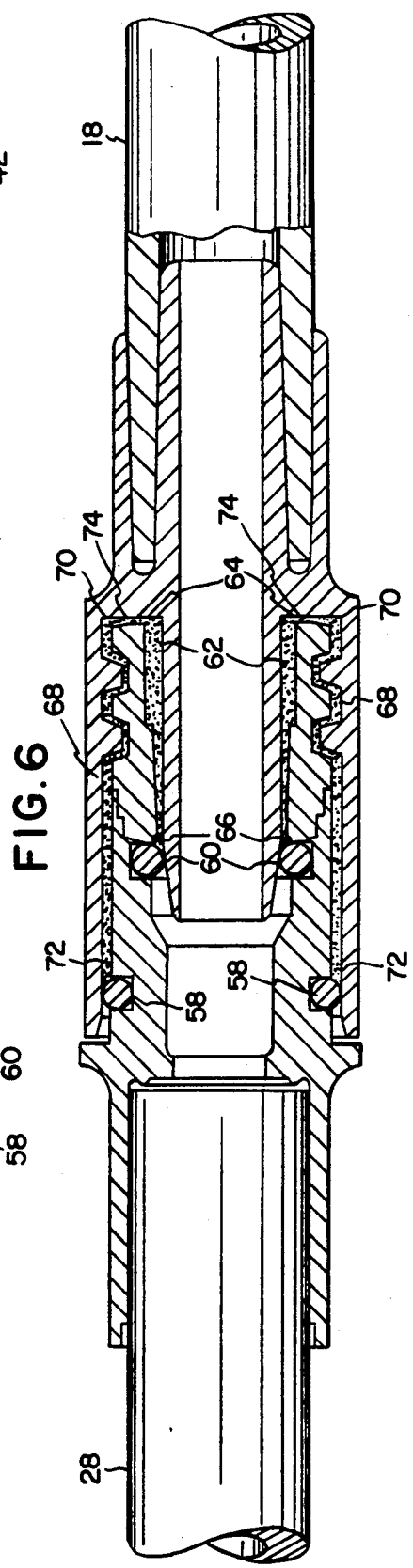
FIG. 6 is a longitudinal view of the male luer and female connector of FIG. 5 shown engaged with the female luer connector and respective tubing defining a continuous fluid passage from tubing to tubing and the sterilizing fluid agent chamber of FIG. 4.

A longitudinal sectional exploded view as shown in FIG. 5 illustrating the male luer connector of FIG. 2 including tubing connection in place with the male luer connector in actual alignment and position for connection with a female luer connector with the cap of FIG. 2 removed, the female luer connector 26 including tubing connection 28. In FIG. 5 the open female luer connector 76 and the open male connector 78 are equivalent to female luer connector 6 or 26 and male connector 8 or 24 of FIG. 1. When the male and female connectors are locked into place as illustrated in FIG. 6, the connectors define a continuous fluid passage from tubing 18 to tubing 28 and the sterilant fluid receiving chamber 74 which contains fluid sterilizing agent liquid 75. In FIG. 6, a longitudinal view is presented of the male luer and female luer connectors locked in place with respective tubing defining a continuous fluid passage from tubing set and the sterilizing fluid agent chamber filled with a measured amount of fluid sterilizing agent. The sterilant fluid receiving chamber 74 of FIG. 6 is the same chamber as defined by FIGS. 3 and 4. In FIG. 3 the chamber is defined by the male luer connector 24 and the female luer connector cap 37. In FIG. 4 the sterilant fluid receiving chamber 74 is shown in isolation, the chamber being defined both in FIG. 3 and FIG. 6, however in FIG. 6 the female luer connector 26 and the male luer connector 24 define the chamber around the connection with both connectors having flexible catheter tubing 28 and 18 respectively completing a continuous conduit for fluids through the connection.

Prior to the present invention the patient would fill the various connectors or spray the various connectors with anti-infective solution before making the connection. The present invention provides a connector which can be filled at the manufacturing location with a measured amount of anti-infective solution and capped off so the patient does not face the task of opening the fluid pathway, and spraying or using liquid droppers apparatus to provide anti-infective treatment of the connectors and then subsequently forming the connection. Not only does the pre-capped anti-infective solution treated connector apparatus according to invention provide simpler procedural steps for the patient, the anti-infective solution is capable of withstanding considerable shelf life through the utilization of suitable elastomeric seal materials which prevent water or other solvent vapor transmission. Furthermore, the pre-capped anti-infective treated connector apparatus can be sterilized by use of gamma radiation to eliminate contamination by organisms resistant to the particular type of anti-infective solution contained in the pre-capped and sealed connector. In addition, the seal materials as well as the materials of construction of the connectors provide a certain degree of inertness to the anti-infective solutions.

The materials of both the seals and the connectors should provide high water or solvent vapor transmission barrier properties in order to maintain the anti-infective solutions substantially constant over long periods of storage. On the other hand, higher viscosity anti-infective solutions can be utilized according to the invention wherein the water or solvent content is substantially reduced before introduction into the capped connector apparatus. Such higher viscosity materials would provide suitable coating of the chamber defined by the cap and the connector and would be less prone to spillage during connection by the patient. Suitable anti-infective solutions include for example, iodine, povidone-iodine, a topical anti-infective although any anti-infective suitable for body catheter contact can be used.

The luer lock connection device according to the invention is comprised of a male luer connector member having a central tubular portion outwardly circumscribed by a generally tubular sheath portion and having an open end facing in a first axial direction which will upon connection, mate with a female luer connector member operatively interconnectable with the male luer connector. The female luer connector having a hollow tubular portion coaxially insertable into said sheath portion which will coaxially receive said central tubular portion of the male luer connector member. Cooperative thread means on the male and female luer connector members provide for releasably locking or holding the members in their operative interconnected orientation. Means are provided for the male and female luer connector members and are responsive to their operative interconnection for forming within the sheath portion, a sterilant fluid receiving chamber, the chamber having an inner annular portion coaxially disposed between the outer side surface of said central tubular portion and the inner side surface of said central tubular portion and the inner side surface of said hollow tubular portion of the female luer connector member. The inner annular portion having an annular first end and an annular second end spaced apart therefrom in the first axial direction. The outer annular portion coaxially disposed between the outer side surface of the hollow tubular portion of said female luer connector member and the inner side surface of the sheath portion, the outer annular portion having an annular first end and an annular second end spaced apart therefrom in said first axial direction. The first ends of the inner and outer annular portions communicating with one another and the sterilant fluid receiving chamber further defined by seal means which are responsive to the operative inner connection of the male and female luer connector members, for forming annular resilient seals around the second ends of the inner and outer annular portions of the chamber.

In another aspect the connector apparatus according to the invention provides for releasably coupling facing end portions of first and second lengths of tubing and communicating their interiors wherein the apparatus is comprised of a first connector member and a second connector member. The first connector member having a hollow, generally tubular configuration, a first end portion, a second end portion operatively connectable to one of the tubing end portions and a cylindrical cavity extending axially inward from the outer end of the first end portion of the first connector member. The cylindrical cavity having an inner end and a hollow tubular male connector portion extending coaxially into said cylindrical cavity from the inner end thereof and being laterally circumscribed by an annular portion of the cylindrical cavity. The second connector member operatively connectable to the first connector member and having a hollow, generally tubular configuration. A first end portion of the second connector member is coaxially insertable into said cylindrical cavity toward the inner end thereof and configurated to coaxially receive said male connector portion. The receiving of the male connector portion is in a radially outwardly spaced relationship therewith and create within the cylindrical cavity a sterilant fluid receiving chamber having an inner annular portion coaxially disposed between the male connector portion and the interior side surface of the firs end portion of the second connector member. In addition, an outer annular portion coaxially disposed between the inner side surface of the first end portion of the first connector member and the outer side surface of the first end portion of the second connector member is defined. The inner and outer annular portions of the sterilant fluid receiving chamber having first ends which are communicated adjacent the inner end of the cylindrical cavity, the second ends which are axially spaced apart from the inner end of the cylindrical cavity and a second end portion operably connectable to the other end of the first and second lengths of tubing. The connector apparatus is physically locked together through cooperating thread means on the first and second connector members for releasably locking the members and their operatively interconnected orientation. The sterilant fluid receiving chamber is sealed and further defined by a first resilient seal means for creating an annular seal at the second end of the outer annular portion of the chamber and a second resilient seal means for creating an annular seal at the second end of the inner annular portion of the chamber.

The prior art luer connectors have provided a diameter bore which tapers inwardly from a distal end, to a diameter that is smaller than the external diameter of a central tubular portion whereby a first liquid seal is stated to result between the external surface of the central tubular portion and the internal wall of the bore of the tubular member. This liquid seal is a pressure engagement between two parts to aid in preventing flow of liquid past the pressure engagement. These prior teachings, e.g., of U.S. Pat. No. 4,346,703 fail to recognize that pressure form fit seals do leak and errode if high precision machining is not applied or if in some way the ailing patient does not properly lock-connect the connectors.

In one illustrative embodiment the '703 patent provides an elastomeric member carried by the female luer connector which is dimensioned and operable for providing a second liquid seal with the internal wall of the rigid outer sheath of the male connector to aid in maintaining a water tight bacteria barrier at the luer lock connection. However, the reference further states that the elastomeric member may be swabbed or the chamber defined by the outer sheath filled with a sterilizing agent by the patient which would aid in preventing contamination of the system.

Any anti-infective material can only be injected by the prior art reference between the first liquid seal formed at the engagement between the exterior surface of a central tubular portion and the interior wall of the bore of the tubular member and the elastomeric seal which provides a single surrounding i.e. cylindrical chamber which can receive anti-infective material.

The present invention provides a U-shaped configurated sterilant fluid receiving chamber which surrounds the elements of the connection through first and second annular chambers which terminate at their respective ends with for example O-ring seal means and which are in communication at the other end of the annular chambers which communicate at their first end portions. The apparatus according to the present invention provides a continuous chamber which is in retrospect a dual chamber terminating at the open ends with O-ring sealing means, the chambers are in communication providing an encirclement anti-infective filled chamber which is clearly shown in FIGS. 3, 4 and 6, with FIG. 4 being an elevated view of the anti-infective solution chamber which is shown in isolation. In addition, the apparatus according to the invention provides the same chamber before use by the patient wherein the chamber is filled during manufacturing with a predetermined amount of an anti-infective solution to file the chamber defined by a luer connection with the female member having a cap over what is normally the tubular connection end portion. When the apparatus is de-capped and the male luer connector is connected to the patient's female luer connector, the chamber is again defined with anti-infective materials contained in the male connector through the connection procedure wherein the solution is forced to conform and fill the defined fluid chamber.

The prior art forces the patient utilizing a catheter means for treatment to perform multiple steps in making a connection to the patient's catheter. Various types of disinfectants and sterilants have been sprayed or utilized through sponge or absorbent clam shell devices at the point in time of connecting the tubing set to the catheter adapter. The present invention provides a very unique sterilant chamber utilizing elastomeric seal means to form in effect a dual chamber, i.e. dual annular chambers which communicate at one end and terminate at the other ends at the elastomeric seal region. In addition, the male connector is shipped to the patient from manufacture wherein the connector is filled with disinfectant and sealed by a sealing cap, i.e. a capped female connector configuration which forms the same chamber. This capped female connector has an inner and outer O-ring seal which prevents the disinfectant from leaking into the sterilant fluid pathway or to the exterior portion of the connector. These two seals and the twist lock mating male and female parts enable the disinfectant to be applied at the point of manufacture, closed and sealed off until the tubing set is connected to either the patient's catheter adapter or a sterile bag of solution. The connector being sealed and incapsulating disinfectant at point of manufacture allows for total sterilization through for example, Gamma radiation of the closed and sealed off connector inclusive of the disinfectant solution. The inventive apparatus not only provides for encapsulation of the disinfectant, it also provides for absolute sterility through Gamma radiation of the connector including encapsulated disinfectant which eliminates any organisms which may be resistive to the particular disinfectant material encapsulated.

As can be seen by the present invention a luer lock connection is provided that is secure and prevents leakage of anti-infective solutions thus preventing contamination which in CAPD could result in peritonitis. Through the embodiments of pre-filling of the luer connector apparatus at the point of manufacture and the providing of dual fluid anti-infective solution chambers which communicate and terminate in a first and second elastomeric seal means which provide chamber means for the external surface portion of the male luer tubular portion and the female luer connector outer side surface. When the male and female connectors are connected, a dual chamber liquid tight bacteria barrier is provided at the luer lock connection. Thus, a double elastomeric seal connection is provided for a dual chamber which surrounds the male/female connectors when joined.

Thus, there has been disclosed a CAPD system and connector apparatus for transferring dialysate fluid to and from the patient which is both safe, simple and easy to use. The apparatus, specifically the connector apparatus, effectively prevents infection of the peritoneal cavity while CAPD or other treatment of the peritoneal cavity is in use. In addition, the connector apparatus provides an effective infection prevention technology to any catheter applications requiring reconnectable fluid flow of medication or body fluids.

Obviously, many modifications and variations of the present invention are possible in light of the above teachings. It is to be understood that the scope of the invention is to be limited only by interpretation of the appended claims.

What is claimed is:

1. A luer lock connection device comprising:
   a male luer connector member having a central tubular portion outwardly circumscribed by a generally tubular sheath portion and having an open end facing in a first axial direction;
   a female luer connector member operatively interconnectable with said male luer connector and having a hollow tubular portion coaxially insertable into said sheath portion to coaxially receive said central tubular portion of said male luer connector member;
   cooperating thread means on said male and female luer connector members for releasably holding them in their operatively interconnected orientation; and
   means associated with said male and female luer connector members and responsive to their operative interconnection for forming within said sheath portion a sterilant fluid-receiving chamber having:
   an inner annular portion coaxially disposed between the outer side surface of said central tubular portion and the inner side surface of said central tubular portion and the inner side surface of said hollow tubular portion of said female luer connector member, said inner annular portion having an annular first end and an annular second end spaced apart therefrom in said first axial direction, and
   an outer annular portion coaxially disposed between the outer side surface of said hollow tubular portion of said female luer connector member and the inner side surface of said sheath portion, said outer annular portion having an annular first end, and an annular second end spaced apart therefrom in said first axial direction, said first ends of said inner and outer annular portions communicating with one another; and
   seal means, responsive to the operative interconnection of said male and female luer connector members, for forming annular resilient seals around said second ends of said inner and outer annular portions of said sterilant fluid-receiving chamber.

2. The luer lock connection device of claim 1 wherein: said chamber is filled with a sterilant fluid.

3. The luer lock connection device of claim 2 wherein: said sterilant fluid contains iodine.

4. The luer lock connection device of claim 1 wherein said seal means include:
   a first resilient seal means exteriorly carried by said hollow tubular portion of said female luer connector member, and
   a second resilient seal means interiorly carried by said hollow tubular portion of said female luer connector member.

5. The luer lock connector device of claim 4 wherein the first resilient seal means and the second resilient seal means are comprised of O-ring seal members.

6. Connector apparatus for releasably coupling facing end portions of first and second lengths of tubing and communicating their interiors, said connector apparatus comprising:
   a first connector member having:
   a hollow, generally tubular configuration,
   a first end portion,
   a second end portion operably connectable to one of said tubing end portions,
   a cylindrical cavity extending axially inwardly from the outer end of said first end portion of said first connector member, said cylindrical cavity having an inner end, and
   a hollow tubular male connector portion extending coaxially into said cylindrical cavity from said inner end thereof and being laterally circumscribed by an annular portion of said cylindrical cavity;
   a second connector member operably connectable to said first connector member and having:
   a hollow, generally tubular configuration,
   a first end portion coaxially insertable into said cylindrical cavity toward said inner end thereof and configured to coaxially receive said male connector portion, in a radially outwardly spaced relationship therewith, and create within said cylindrical cavity a sterilant fluid-receiving chamber having an inner annular portion coaxially disposed between said male connector portion and the interior side surface of said first end portion of said second connector member, and an outer annular portion coaxially disposed between the inner side surface of said first end portion of said first connector member and the outer side surface of said first end portion of said second connector member, said inner and outer annular portions of said sterilant fluid-receiving chamber having first ends which are communicated adjacent said inner end of said cylindrical cavity, said second ends which are axially spaced apart from said inner end of said cylindrical cavity, and
   a second end portion operably connectable to the other of said first and second lengths of tubing;
   thread means on said first and second connector members for releasably locking them in their operatively interconnected orientation;
   first resilient seal means for creating an annular seal at said second end of said outer annular portion of said sterilant fluid-receiving chamber; and
   second resilient seal means for creating an annular seal at said second end of said inner annular portion of said sterilant fluid-receiving chamber.

7. The connector apparatus of claim 6 wherein: said chamber is filled with a sterilant fluid.

8. The connector apparatus of claim 6 wherein: said sterilant fluid contains iodine.

9. The connector apparatus of claim 6 comprising said chamber and sterilant fluid is exposed to gamma radiation.

10. The connector apparatus of claim 6 wherein:
said first resilient seal means include a first O-ring seal member, and
said second resilient seal means include a second O-ring seal member.

11. The connector apparatus of claim 6 wherein:
said first O-ring seal member is exteriorly carried by said second connector member, and
said second O-ring seal member is internally carried by said second connector member.

12. In a tubing set for use with equipment for Continuous Ambulatory Peritoneal Dialysis in which a solution container is coupled via the tubing set to a patient's tube that communicates with a patient's peritoneal cavity, and with the solution container having a transport port carrying a luer connector and the patient's tube carrying a luer connector, the improvement comprising:
a male luer connector member having a central tubular portion outwardly circumscribed by a generally tubular sheath portion and having an open end facing in a first axial direction;
a female luer connector member operatively interconnectable with said male luer connector and having a hollow tubular portion coaxially insertable into said sheath portion to coaxially receive said central tubular portion of said male luer connector member;
cooperating thread means on said male and female luer connector members for releasably holding them in their operatively interconnected orientation; and
means associated with said male and female luer connector members and responsive to their operative interconnection for forming within said sheath portion a sterilant fluid-receiving chamber having:
an inner annular portion coaxially disposed between the outer side surface of said central tubular portion and the inner side surface of said central tubular portion and the inner side surface of said hollow tubular portion of said female luer connector member, said inner annular portion having an annular first end and an annular second end spaced apart therefrom in said first axial direction, and
an outer annular portion coaxially disposed between the outer side surface of said hollow tubular portion of said female luer connector member and the inner side surface of said sheath portion, said outer annular portion having an annular first end, and an annular second end spaced apart therefrom in said first axial direction, said first ends of said inner and outer annular portions communicating with one another; and
seal means, responsive to the operative interconnection of said male and female luer connector members, for forming annular resilient seals around said second ends of said inner and outer annular portions of said sterilant fluid-receiving chamber.

13. In a tubing set for use with equipment for Continuous Ambulatory Peritoneal Dialysis in which a solution container is coupled via the tubing set to a patient's tube that communicates with a patient's peritoneal cavity, and with the solution container having a transport port carrying a luer connector and the patient's tube carrying a luer connector, the improvement comprising:
a first connector member having:
a hollow, generally tubular configuration,
a first end portion,
a second end portion operably connectable to one of said tubing end portions,
a cylindrical cavity extending axially inwardly from the outer end of said first end portion of said first connector member, said cylindrical cavity having an inner end, and
a hollow tubular male connector portion extending coaxially into said cylindrical cavity from said inner end thereof and being laterally circumscribed by an annular portion of said cylindrical cavity;
a second connector member operably connectable to said first connector member and having:
a hollow, generally tubular configuration,
a first end portion coaxially insertable into said cylindrical cavity toward said inner end thereof and configured to coaxially receive said male connector portion, in a radially outwardly spaced relationship therewith, and create within said cylindrical cavity a sterilant fluid-receiving chamber having an inner annular portion coaxially disposed between said male connector portion and the interior side surface of said first end portion of said second connector member, and an outer annular portion coaxially disposed between the inner side surface of said first end portion of said first connector member and the outer side surface of said first end portion of said second connector member, said inner and outer annular portions of said sterilant fluid-receiving chamber having first ends which are communicated adjacent said inner end of said cylindrical cavity, said second ends which are axially spaced apart from said inner end of said cylindrical cavity, and
a second end portion operably connectable to the other of said first and second lengths of tubing;
cooperating thread means on said first and second connector members for releasably locking them in their operatively interconnected orientation;
first resilient seal means for creating an annular seal at said second end of said outer annular portion of said sterilant fluid-receiving chamber; and
second resilient seal means for creating an annular seal at said second end of said inner annular portion of said sterilant fluid-receiving chamber.

14. A luer lock connection device comprising:
a male luer connector member having a central tubular portion outwardly circumscribed by a generally tubular sheath portion and having an open end facing in a first axial direction;
a female luer connector member operatively interconnectable with said male luer connector and having a hollow tubular portion coaxially insertable into said sheath portion to coaxially receive said central tubular portion of said male luer connector member;
cooperating thread means on said male and female luer connector members for releasably holding them in their operatively interconnected orientation; and
means associated with said male and female luer connector members and responsive to their operative interconnection for forming within said sheath portion a sterilant fluid-receiving chamber having:

an inner annular portion coaxially disposed between the outer side surface of said central tubular portion and the inner side surface of said central tubular portion and the inner side surface of said hollow tubular portion of said female luer connector member, said inner annular portion having an annular first end and an annular second end spaced apart therefrom in said first axial direction, and an outer annular portion coaxially disposed between the outer side surface of said hollow tubular portion of said female luer connector member and the inner side surface of said sheath portion, said outer annular portion having an annular first end, and a annular second end spaced apart therefrom in said first axial direction, said first ends of said inner and outer annular portions communicating with one another;

seal means, responsive to the operative interconnection of said male and female luer connector members, for forming annular resilient seals around said second ends of said inner and outer annular portions of said sterilant fluid-receiving chamber; and the female luer connector member having a hollow tubular end portion remote from the hollow tubular portion coaxially insertable into the sheath portion of the male luer connector wherein the removed hollow tubular end portion is capped by a capping means.

15. A method for avoiding patient catheter fluid inflow contamination in CAPD by providing a connector device having a sterilant fluid receiving chamber comprising:

filling the chamber during manufacture of the male luer connector with an anti-infective solution which when capped by a female luer connector having a capping means on an outer end portion of a hollow tubular portion aligned axially through the female luer connector, with sufficient fluid to fill the chamber formed by the capped female luer connector and the male luer connector; and maintaining the fluid in a portion of the male luer connector when the capped female luer connector is removed and connecting the fluid containing male luer connector with the patient female luer connector catheter connection redefining the fluid filled sterilant fluid receiving chamber.

16. In a CAPD apparatus in which a solution container is coupled via flexible tubing to a patient's tube that communicates with a patient's peritoneal cavity, the improvement which comprises:

a male luer connector member having a central tubular portion outwardly circumscribed by a generally tubular sheath portion and having an open end facing in a first axial direction;

a female luer connector member operatively interconnectable with said male luer connector and having a hollow tubular portion coaxially insertable into said sheath portion to coaxially receive said central tubular portion of said male luer connector member;

cooperating thread means on said male and female luer connector members for releasably holding them in their operatively interconnected orientation; and means associated with said male and female luer connector members and responsive to their operative interconnection for forming within said sheath portion a sterilant fluid-receiving chamber having:

an inner annular portion coaxially disposed between the outer side surface of said central tubular portion and the inner side surface of said central tubular portion and the inner side surface of said hollow tubular portion of said female luer connector member, said inner annular portion having an annular first end and an annular second end spaced apart therefrom in said first axial direction, and an outer annular portion coaxially disposed between the outer side surface of said hollow tubular portion of said female luer connector member and the inner side surface of said sheath portion, said outer annular portion having an annular first end, and an annular second end spaced apart therefrom in said first axial direction said first ends of said inner and outer annular portions communicating with one another; and seal means, responsive to the operative interconnection of said male and female luer connector members, for forming annular resilient seals around said second ends of said inner and outer annular portions of said sterilant fluid-receiving chamber.

17. In a CAPD apparatus in which a solution container is coupled via flexible tubing to a patient's tube that communicates with a patient's peritoneal cavity, the improvement which comprises:

a first connector member having:
a hollow, generally tubular configuration,
a first end portion,
a second end portion operably connectable to one of said tubing end portions,
a cylindrical cavity extending axially inwardly from the outer end of said first end portion of said first connector member, said cylindrical cavity having an inner end, and
a hollow tubular male connector portion extending coaxially into said cylindrical cavity from said inner end thereof and being laterally circumscribed by an annular portion of said cylindrical cavity;

a second connector member operably connectable to said first connector member and having:
a hollow, generally tubular configuration,
a first end portion coaxially insertable into said cylindrical cavity toward said inner end thereof and configured to coaxially receive said male connector portion, in a radially outwardly spaced relationship therewith, and create within said cylindrical cavity a sterilant fluid-receiving chamber having an inner annular portion coaxially disposed between said male connector portion and the interior side surface of said first end portion of said second connector member, and an outer annular portion coaxially disposed between the inner side surface of said first end portion of said first connector member and the outer side surface of said first end portion of said second connector member, said inner and outer annular portions of said sterilant fluid-receiving chamber having first ends which are communicated adjacent said inner end of said cylindrical cavity, said second ends which are axially spaced apart from said inner end of said cylindrical cavity, and a second end portion operably connectable to the other of said first and second lengths of tubing;

cooperating thread means on said first and second connector members for releasably locking them in their operatively interconnected orientation;

first resilient seal means for creating an annular seal at said second end of said outer annular portion of said sterilant fluid-receiving chamber; and second resilient seal means for creating an annular seal at said second end of said inner annular portion of said sterilant fluid-receiving chamber.

* * * * *